United States Patent [19]
Kessler

[11] Patent Number: 5,603,715
[45] Date of Patent: Feb. 18, 1997

[54] MEDULLARY PIN

[76] Inventor: Sigurd Kessler, Am Mühlanger 70, Puchheim, Germany, 82178

[21] Appl. No.: 308,095

[22] Filed: Sep. 16, 1994

[51] Int. Cl.⁶ .................................................. A61B 17/72
[52] U.S. Cl. ................................................ 606/63; 606/62
[58] Field of Search .................................. 606/62, 63, 64, 606/65, 66, 67, 68

[56] References Cited

U.S. PATENT DOCUMENTS

| | | | |
|---|---|---|---|
| 2,998,007 | 8/1961 | Herzog | 606/63 |
| 4,467,793 | 8/1984 | Ender | 606/62 |
| 4,794,919 | 1/1989 | Nilsson | 606/65 |
| 5,057,103 | 10/1991 | Davis | 606/68 |

FOREIGN PATENT DOCUMENTS

| | | |
|---|---|---|
| 0095990 | 12/1983 | European Pat. Off. . |
| 0381462A3 | 8/1990 | European Pat. Off. . |
| 2141020 | 1/1973 | France . |
| 2243673 | 4/1975 | France . |
| 0029752 | 6/1981 | France . |
| 2484243 | 12/1981 | France . |
| 1054659 | 4/1959 | Germany . |
| 2821785 | 11/1979 | Germany . |
| 8330389 U | 9/1985 | Germany . |
| 8809715 U | 12/1988 | Germany . |
| 4002400A1 | 8/1991 | Germany . |

*Primary Examiner*—Michael Powell Buiz
*Assistant Examiner*—Scott B. Markow
*Attorney, Agent, or Firm*—Townsend and Townsend and Crew LLP

[57] ABSTRACT

A medullary pin is described for intermedullary use in the healing of damage to bones, in particular the healing of fractures of tubular bones. The medullary pin is insertable into the medullary tube of the bone and can be secured to the bone with fixation means at both ends. At least one end of the pin is formed as a fastening part which can be fixed to the outer side of the bone.

15 Claims, 5 Drawing Sheets

MEDULLARY PIN

FIELD OF INVENTION

The invention relates to a medullary pin for intermedullary use in the healing of bone damage, in particular of fractures of tubular bones, the medullary pin being insertable into the medullary cavity of the bone and being securable at both ends to the bone with fixation means. Furthermore, a method of using such a medullary pin is described.

BRIEF DESCRIPTION OF THE PRIOR ART

Pins of this kind are normally used in the treatment of tubular bones, either when it must be assumed that the fracture will not grow together, or not grow together sufficiently well by simple immobilization, or if a long period of immobilization, which as a rule amounts to 8 to 12 weeks, cannot be tolerated.

Pins of the above named kind are inserted into the medullary cavity of the bone and are fixed to the bone on both sides of the bone damage by means of transverse pins. A medullary pin of this kind is known from DE-OS 40 02 400. In accordance with this laying open print, the transverse pins are formed as bone screws. For the connection of the bone screws with the medullary pin, which as been inserted into the medullary cavity, it is necessary to drill the bone on both sides of the fracture.

In order to be able to guarantee the correct positioning of the screws in the holes, the bores must be made by means of complicated aiming devices or by using X-ray observation.

Fractures, which lie very close to one end of the bone, cannot be treated with these pins, because a fixation on both sides of the fracture is not possible.

Medullary pins are also known in which the fixation of the pin via the transverse pins has been dispensed with. In these pins the fixation of the pin in the bone is for example achieved in that the pin has a sharp-edged tip which is driven into the bone material at the end of marrow cavity. This connection is however not very durable and customarily loosens after only a few days through the movements during the carrying.

PRINCIPAL OBJECT OF THE INVENTION

The object of the invention is to so form a medullary pin for intermedullary use in the hoaling of bone damage so that a simple and at the same time secure anchoring of the medullary pin in the bone is guaranteed, and so that a maximum extension of the length of bone being treated is possible. The arrangement should be such that both a static and also a dynamic locking is possible for the treatment of oblique and transverse fractures. Furthermore, it is the object to set forth a method of using a medullary pin in accordance with the invention.

BRIEF SUMMARY OF THE INVENTION

This object is satisfied in accordance with the invention in that at least one end of the medullary pin is formed as a fastening part which can be fixed to the outer side of the bone.

The object set forth above is thus solved in advantageous manner through the use of a medullary pin which can be fixed to the outer side of the bone.

In accordance with an expedient embodiment, the fastening part is formed as a separate part which is secured to one end of the medullary pin, and in particular screwed thereto. In this arrangement the fastening part and the medullary pin can be placed against one another and connected to one another by means of screws. However, one end of the fastening part and of the medullary pin can, in each case, be provided with a thread in such a way that the two parts can be screwed to one another at their end faces.

Several advantages can be achieved through this separate formation of the fastening part. By way of example, medullary pins of different lengths can be connected to and used with one and the same fastening part. Furthermore, the fastening part and the medullary pin can be so formed and connected to one another that they can be used both for right limbs and also for left limbs. The connection location between the fastening part and the medullary pin can, with this arrangement, lie both inside and also outside of the bone.

In a further embodiment of the invention, the end of the medullary pin facing the fastening part is made wider than the remaining part of the medullary pin. A connection of the medullary pin with the fastening part can, for example, take place by a threaded connection; the end of the medullary pin facing the fastening part can at least have one bore for receiving the corresponding screw. When the end of the medullary pin facing the fastening part is already located outside of the medullary cavity, it is expedient to make this end wider than the remaining part of the medullary pin in order, through the use of additional material, to re-establish, or indeed exceed the stability of the medullary pin which has been lost through the bore.

In accordance with a further preferred embodiment the fastening part is formed as a distance piece for the fixation of the medullary pin to the bone, with the distance piece being rotationally fixedly connected to the medullary pin. The rotationally fixed connection can for example be achieved by a toothed crown between the distance piece and the medullary pin. The distance piece is preferably formed as a sleeve which has formations at one end for fixation to the bone, for example via screws. The distance piece is preferably connected to the medullary pin via a screw extending through the sleeve.

With a fixation of the two ends of the medullary pin to the bone via rotationally fixed connections, a static locking is provided which prevents mutual rotation or tilting of the bone parts relative to one another, and thus a tendency of the bone to shorten, so that oblique or comminuted fractures can also be treated.

In accordance with a further advantageous embodiment, the medullary pin is formed as a hollow pin which has an inner cavity open at both ends, with the open end of the medullary pin lying opposite to the fastening part having an internal or external thread.

In accordance with a further preferred embodiment, a screw with an external or internal thread is mounted at the open end of the medullary pin opposite to the fastening part for the fixation from the outside of the medullary pin inserted into the medullary cavity. The screw is thereby preferably formed as a hollow screw and the head of the screw preferably contacts the bone from the outside via a washer. In this way the head is prevented from breaking into the bone. The free end of the medullary pin can be fixed in the bone via the screw and, at the same time, a predetermined pressure for pressing the fracture surfaces together can be set through the use of the screw as a tension screw.

Through this dynamic locking an ideal healing action is made possible at the same time as a minimal pain development with transverse fractures.

The washer is preferably so formed that it contacts the outer side of the bone over its whole surface in order to thereby ensure a reliable seat at the bone.

In accordance with a further preferred embodiment, a terminal cap formed as a tip is secured by a screw connection to the open end of the medullary pin lying opposite to the fastening part. The terminal cap thereby has lateral exit openings which communicate via channels with the inner space of the medullary pin when the terminal cap is screwed onto the end of the medullary pin. Spike wires are displaceably arranged in the interior space of the medullary pin. Their ends adjacent the terminal cap can be displaced through the exit openings via the channels and their ends adjacent the securing part can be secured to the latter. The securing of the spike wires to the securing part preferably takes place via a clamping screw.

In accordance with a preferred method for the use of a medullary pin in accordance with the invention, the bone is first drilled into one side of the fracture, either centrally or laterally. The end of the medullary pin opposite to the fastening part is introduced into the medullary cavity through this first bore and, after complete insertion of the medullary pin, the fastening part is fixed to the bone, in particular screwed thereto. Through this fixation of the medullary pin to the bone from the outside the normally required aiming device or the drilling of the bores while observing them on the X-ray screen are avoided, which leads to a substantial simplification of the fixation of the medullary pin to the bone.

Through the fixation of the medullary pin to the massive bone end, a very stable anchorage of the medullary pin to the bone is simultaneously provided.

In a further preferred embodiment, the bone is drilled into on both sides of the fracture and the end of the medullary pin lying opposite to the fastening part is fixed in the bone by means of the screw inserted through the second bore, or by means of the distance piece and the screw.

With this arrangement this second bore is preferably formed laterally outside of the extension of the medullary cavity, so that, for example when treating an upper arm fracture, the second bore does not pass in the customary manner vertically from above through the shoulder joint, but is rather directed obliquely from the side. In this way, a bore through the tendons is prevented, so that injury to the tendons and the protracted rehabilitation processes which are caused thereby are avoided.

In accordance with another preferred embodiment, a guide wire is introduced into the bone, prior to introduction of the medullary pin, so that its two ends extend outwardly through the first bore and the second bore respectively. The hollow medullary pin is then introduced via the guide wire through the first bore, and the hollow screw, or the distance piece and the screw, are introduced into the bone through the second bore via the guide wire, whereby a particularly simple screw connection of the medullary pin with the screw is made possible.

In accordance with a further preferred embodiment of the method, the spike wires are so pushed into the medullary pin, prior to its full introduction into the bone, that they emerge through the exit openings in the terminal cap and penetrate into the bone material. After sufficient penetration of the spike wires into the bone material the ends of the spike wires adjacent the fastening part are secured to the latter and the medullary pin is subsequently fully introduced into the bone, so that the ends of the spike wires which stick into the bone material are tilted or bent relative to the medullary pin and adopt a substantially perpendicular position to the longitudinal axis of the bone. After full insertion of the medullary pin, the fastening part is fixed to the bone.

When carrying out this method, the bone must only be drilled at one position and the tilting of the spike wires relative to the medullary pin results in a very stable anchoring of the medullary pin in the bone material.

Further particular advantageous features of the invention are set forth in the subordinate claims.

The advantage of a medullary pin formed in accordance with the invention, and of the method of using this medullary pin lies, on the one hand, in the reliable and stable anchoring of the medullary pin, with the bone, and this fixation of the medullary pin to the bone can be effected very simply from the outside. On the other hand, a maximum extension of the length of bone to be treated is ensured since the bores can be placed right up to the ends of the bone.

Moreover, both oblique fractures and comminuted fractures and also transverse fractures can be treated by the selective formation as a static or dynamic locking system. An additional advantage is the fact that the contact pressure at the positions of the fractures can be so set via the tension screw that an ideal healing action can be set up with simultaneously minimal pain burden.

A further advantage of the invention is the modular assembly of the medullary pin. Through a simple formation of the medullary pin as a tube with two threads at its ends, the different fittings (fastening part, distance piece, screw with washer, terminal cap) can be ideally combined with one another depending on the injury that is present. Moreover, the quantity of the parts which must normally be stored in, or in the immediate vicinity of, the operating theatre is significantly reduced, whereby both the space and also the costs for the storage can be reduced.

BRIEF DESCRIPTION OF THE DRAWINGS

The invention will be explained in the following with reference to an embodiment and to the following drawings.

DESCRIPTION OF PREFERRED EMBODIMENTS

Figure 1:
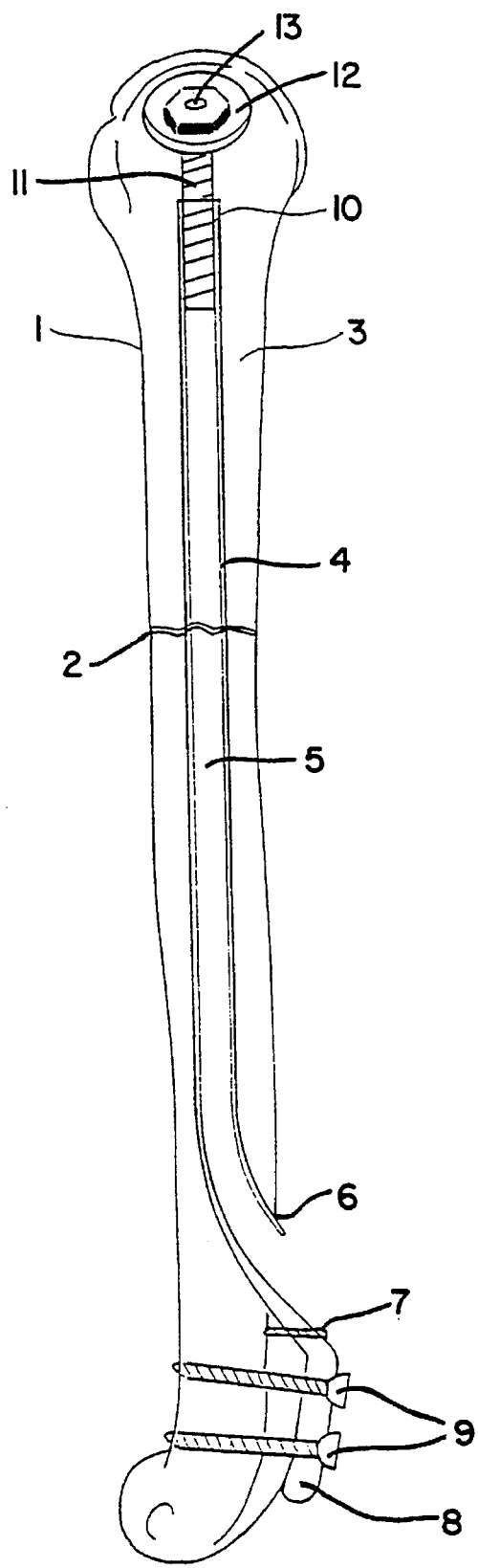
FIG. 1 is a side view of an upper arm bone in part section with a medullary pin formed in accordance with the invention.

FIG. 1 shows a bone 1 with a fracture 2. A medullary pin 4 formed in accordance with the invention is inserted into the medullary cavity 3 of the bone. The medullary pin 4 is formed as a hollow pin which has an inner space 5 open at both ends. The bone 1 illustrated in FIG. 1 is an upper arm bone with a transverse fracture.

The lower end of the medullary pin emerges laterally through a first bore 6 at the lower end of the bone 1 and is connected via screw 7 with a first fastening part 8. The fastening part 8 contacts the outer side of the bone 1 and is fixed to the latter by means of screws 9.

An inner thread 10 is formed at the upper end of the medullary pin 4 and a screw 11 is screwed into this inner thread 10. The head of the screw 11 thereby contacts the outer side of the upper end of the bone 1 via a washer 12. The screw 11 is formed as a hollow screw and has an opening 13 in its head.

Figure 2:
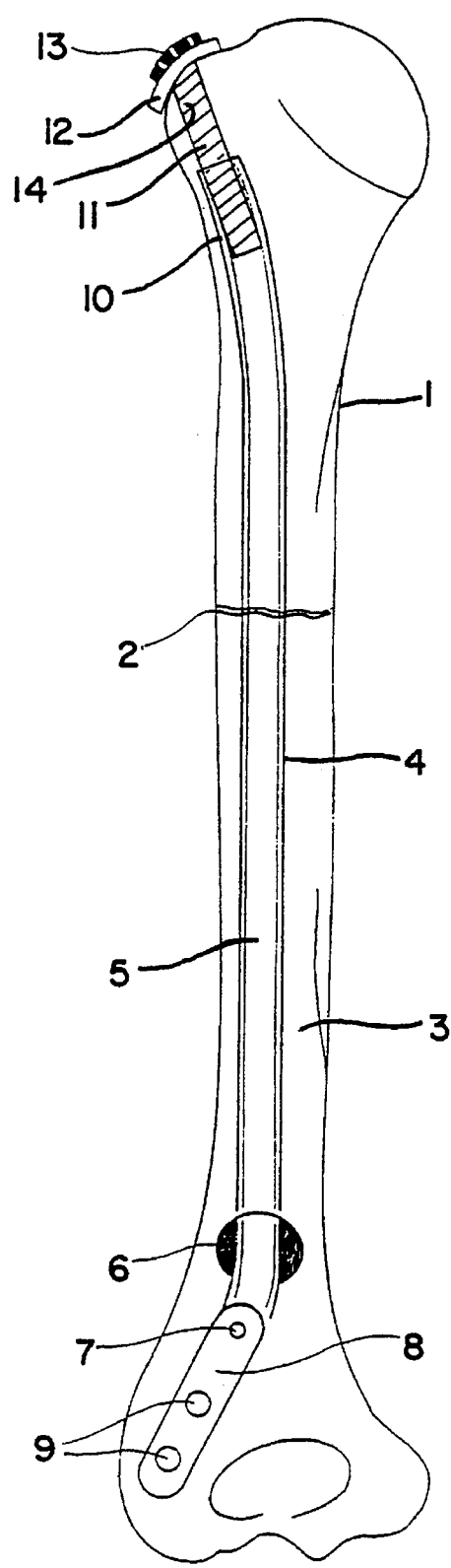
FIG. 2 is a front view of an upper arm bone in partial section with a medullary pin formed in accordance with the invention.

FIG. 2 shows a front view of the illustration of FIG. 1. From this one can see that the screw 11 penetrates into the bone 1 via a second bore 14, and that the washer 12 prevents the head of the screw 11 breaking into the second bore 14. The washer 12 is so shaped that it contacts the outer side of the bone 1 over its whole surface.

The medullary pin 4 of the invention in accordance with FIGS. 1 and 2 forms a dynamic lock with which preferably transverse fractures can be treated.

For the introduction of the medullary pin 4 into the medullary cavity 3 of the bone 1, the bone 1 is first drilled into at its lower and upper ends, so that the medullary cavity 3 opens outwardly at the side via the first bore 6 at its lower end and opens outwardly at the side via the second bore 14 at its upper end. A guide wire is subsequently introduced into the bone 1 through the two bores 6, 14.

The medullary pin 4 is introduced via the first bore 6 into the medullary cavity 3 from the bottom via the guide wire, until the fastening part 8 contacts the lower outer side of the bone 1. The screw 11 is introduced through the second bore 14 via the guide wire and is screwed to the medullary pin 4 via the inner thread 10. The screw connection is thereby so tightened that an ideal connection of the bone pieces results at the position of the fracture 2.

Figure 3:
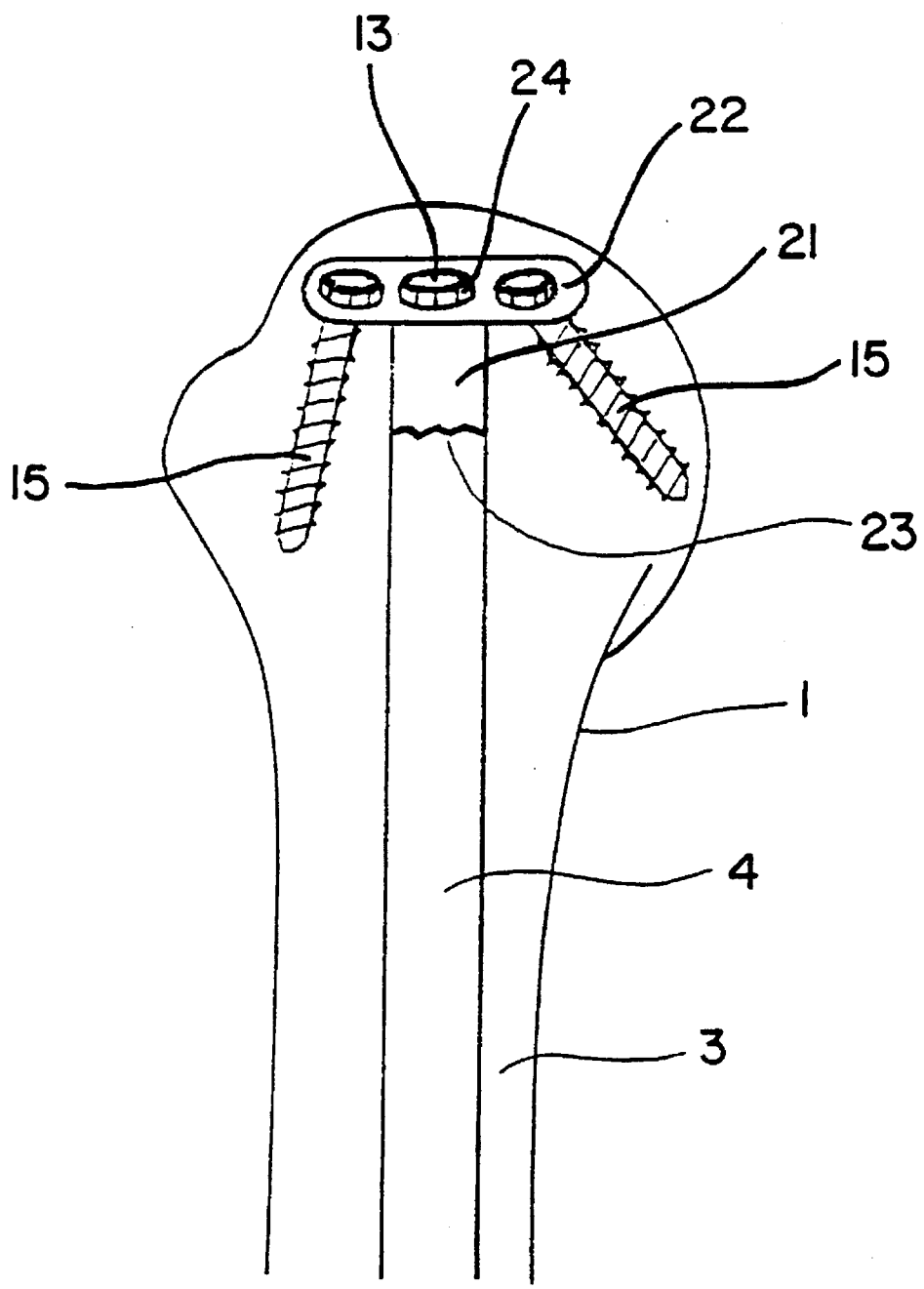
FIG. 3 shows the upper end of an upper arm bone with a medullary pin formed in accordance with the invention and secured via a distance piece.

In FIG. 3 a distance piece 21 is arranged at the upper end of the medullary pin 4 in place of the washer 12. The distance piece 21 is secured via formations 22 to the bone 1 with screws 15 and has at its lower end a toothed crown 23. This toothed crown 23 engages into a corresponding toothed arrangement at the end of the medullary pin 4 and thus prevents rotation of the distance piece 21 relative to the medullary pin 4.

The distance piece 21 is formed as a sleeve and is screwed to the medullary pin 4 via a screw 24 which extends through the sleeve. The screw 24 is formed as a hollow screw, as is the screw 11 in FIGS. 1 and 2, and has an opening 13 in its head.

For the fixation of the medullary pin 4 both the distance piece 21 and also the screw 24 are guided through the second bore 14 analogously to the screw 11 of FIGS. 1 and 2 via a guide wire.

Through the use of the distance piece 21, a static lock is provided with which oblique fractures and comminuted fractures, i.e. fractures with a tendency to shorten, can be treated, since the fixation of the medullary pin 4 in a fixed position at both ends prevents mutual displacement, rotation and tilting of the bone fragments.

Figure 4C:
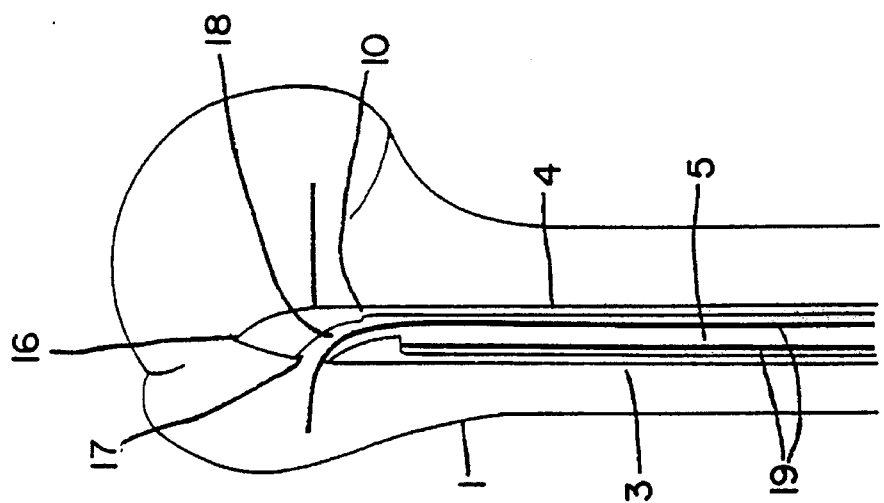
FIGS. 4A–4C are three different views showing different positions of a medullary pin formed in accordance with the invention during the insertion process into a bone.
Figure 4B:
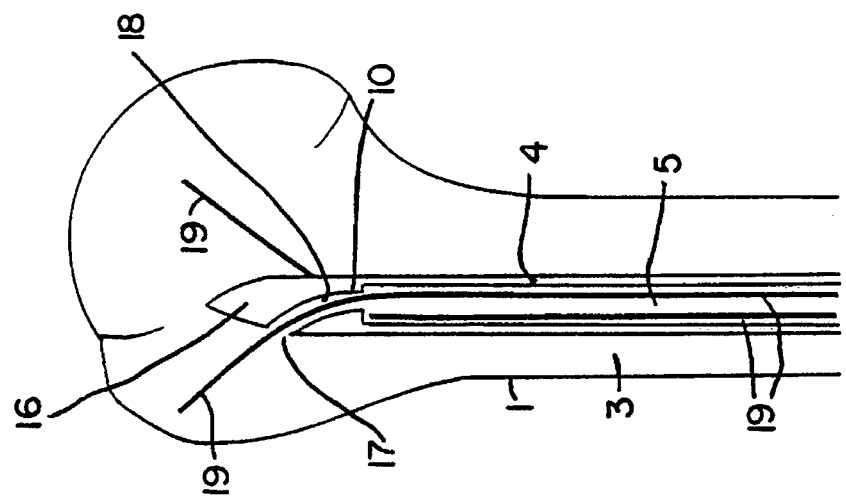
Figure 4A:
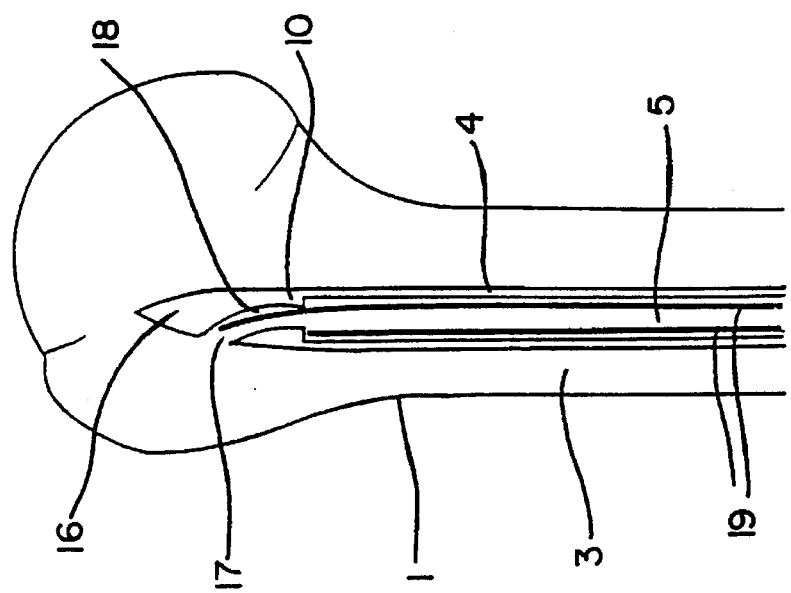

FIGS. 4A–4C show a further embodiment of a medullary pin 4 formed in accordance with the invention. In this arrangement a terminal cap 16 formed as a tip or point is screwed to the medullary pin 4 via the internal thread 10. The terminal cap 16 has exit openings 17 which communicate via channels 18 with the inner space 5 of the medullary pin 4.

Spike wires 19 are arranged in the interior space 5 of the medullary pin 4 and their ends adjacent the terminal cap 16 are displaceable through the exit openings 17 via the channels 10.

In FIG. 4A the spike wires are fully arranged within the medullary pin 4 and in the channels 18, while in FIGS. 4B–4C the spike wires have been pushed out of the medullary pin 4 through the exit openings 17.

Figure 5:
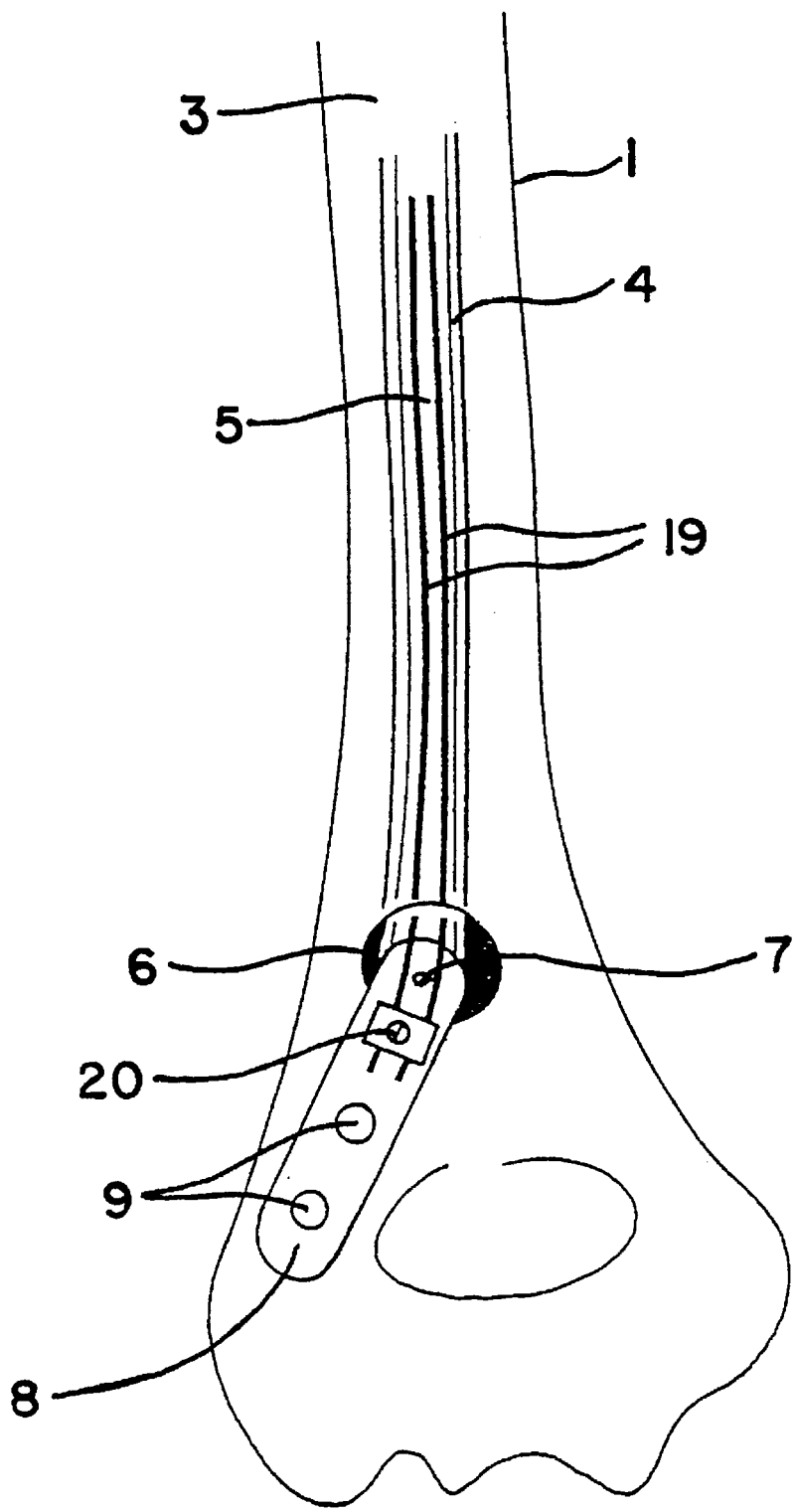
FIG. 5 illustrates the securing of two spike wires to a fastening part of the medullary pin formed in accordance with the invention.

In FIG. 5 the lower ends of the spike wires 19 are secured to the fastening part 8 via a clamping screw 20.

For the introduction of a medullary pin 4 in accordance with the embodiment of FIGS. 4A–4C and 5, the spike wires 19 are pushed into the medullary pin 4 from below, prior to complete introduction of the medullary pin 4, i.e. on reaching the position of the medullary pin 4 of FIG. 4A, in such a way that they emerge through the exit opening 17 in the terminal cap 16 and penetrate into the bone material (FIG. 4B).

After sufficient penetration of the spike wires into the bone material (FIG. 4B), the lower ends of the spike wires 19 are fixed to the fastening part 8 via the clamping screw 20.

The medullary pin 4 is finally fully introduced into the bone 1, so that the ends of the spike wires 19 which stick into the bone material are tilted relative to the medullary pin 4 and adopt a substantially perpendicular position to the longitudinal direction of the bone 1 (FIG. 4C). After the full introduction of the medullary pin 4 the fastening part 8 is fixed to the bone 1 with the screws 9.

Figure 6:
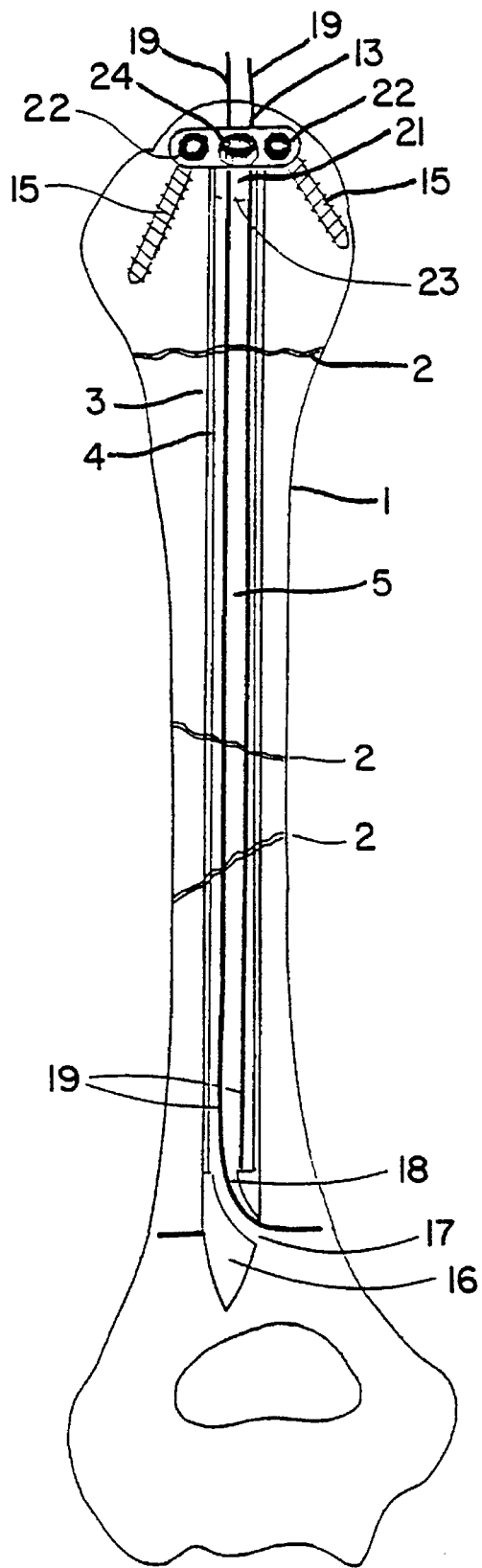
FIG. 6 shows a medullary pin formed in accordance with the invention which is secured via a distance piece and spike wires.

FIG. 6 shows a bone 1 with a plurality of fractures 2 which partly extend obliquely and are partly disposed very close to the end of the bone. A medullary pin 4 in accordance with the invention is inserted into the bone 1 and is fixed to the bone 1 at its upper end via the distance piece 21 and its lower end via the spike wires 19. The spike wires 19 can be secured to the distance piece 21 with a clamping screw 20, which is not shown but is analogous to that of FIG. 5.

Through this combination of different types of connection a static lock is provided with which preferably oblique fractures and comminuted fractures can be treated. In addition, the fracture location 2 which is disposed very close to the end of the bone can be treated by introduction of the medullary pin 4 from above.

What is claimed is:

1. A medullary pin for intermedullary use in the healing of a fractured tubular bone having a medullary cavity and an outer side, said pin having an inner space, a first end and an open second end, said pin being insertable into the medullary cavity of the bone, the first end of said medullary pin including a fastening part fixable to the outer side of the bone, a terminal cap at the open second end of said medullary pin located remote from said fastening part, said terminal cap having at least one exit opening which is lateral relative to a longitudinal axis of said medullary pin and communicates via a channel with an inner space of said medullary pin, at least one spike wire having first and second ends and displaceably arranged in said inner space of said medullary pin, said first end of said spike wire adjacent said terminal cap being displaceable through said at least one exit opening via said channel, and said second end of said spike wire adjacent said fastening part being securable to the fastening part, and means for securing said at least one spike wire to the fastening part.

2. Medullary pin in accordance with claim 1, wherein said fastening part has holes for fixation to said bone.

3. Medullary pin in accordance with claim 2, wherein said fastening part has two holes for fixation to said bone.

4. Medullary pin in accordance with claim 1, wherein said fastening part comprises a separate part which is secured to the first end of said medullary pin.

5. Medullary pin in accordance with claim 4, including screw fastening means for screwing said fastening part to said medullary pin.

6. Medullary pin in accordance with claim 1, wherein the first end of the medullary pin adjacent said fastening part is wider than a remaining part of said medullary pin.

7. Medullary pin in accordance with claim 1, wherein said fastening part comprises a distance piece which is fixable to said bone and rotationally fixedly connectable to said medullary pin.

8. Medullary pin in accordance with claim 1, wherein said medullary pin comprises a hollow pin which has an inner cavity which includes the inner space and which is open at said first and second ends of said medullary pin, at least the open end of said medullary pin remote from said fastening part being threaded.

9. Medullary pin in accordance with claim 1, wherein said at least one exit opening of said terminal cap comprises first and second exit openings, and said at least one spike wire includes first and second spike wires arranged in said inner space of said medullary pin.

10. A medullary pin for intermedullary use in the healing of a fractured tubular bone having a medullary cavity and an outer side, said pin having an inner space, a first end and an open second end, said pin being insertable into the medullary cavity of the bone, the first end of said medullary pin including a fastening part fixable to the outer side of the bone, a terminal cap at the open second end of said medullary pin located remote from said fastening part, said terminal cap having at least one exit opening which is lateral relative to a longitudinal axis of said medullary pin and communicates via a channel with the inner space of said medullary pin, and wherein the first end of the medullary pin adjacent said fastening part is wider than a remaining part of said medullary pin.

11. Medullary pin in accordance with claim 10 including at least one spike wire having first and second ends and displaceably arranged in said inner space of said medullary pin, said first end of said spike wire adjacent said terminal cap being displaceable through said at least one exit opening via said channel, and said second end of said spike wire adjacent said fastening part being securable to the fastening part.

12. Medullary pin accordance with claim 11, including means for securing said at least one spike wire to the fastening part.

13. Medullary pin in accordance with claim 1, wherein said means for securing said at least one spike wire comprises a clamping screw.

14. Method for using a medullary pin on a fractured bone having a medullary cavity and an outer side, the method comprising the steps of providing a medullary pin having an inner space, a first end and an second open end, the first end of said medullary pin including a fastening part fixable to the outer side of the bone, and a terminal cap at the open second end of said medullary pin having at least one exit opening which is lateral relative to a longitudinal axis of the medullary pin and which communicates via a channel with the inner space of said medullary pin; drilling said bone on at least one side of the fracture to form a first bore; introducing said second end of said medullary pin remote from said fastening part through said first bore into the medullary cavity; pushing at least one spike wire into the inner space of said medullary pin such that a first end of the spike wire emerges through said at least one exit opening in said terminal cap and penetrates into the bone; after sufficient penetration of said first end of the at least one spike wire into the bone, securing a second end of said at least one spike wire adjacent said fastening part to the fastening part; further moving said medullary pin into its final position in said medullary cavity of said bone whereby a portion of said first end of said at least one spike wire which penetrates into said bone becomes angularly inclined relative to a longitudinal direction of the bone; and fixing said fastening part to the bone after said medullary pin has been moved into said final position in said medullary cavity.

15. Method in accordance with claim 14, wherein said fixing step comprises providing a screw and securing said fastening part to said bone with the screw.

* * * * *